United States Patent
Matsumoto

(10) Patent No.: US 8,691,957 B2
(45) Date of Patent: Apr. 8, 2014

(54) SWELLABLE CROSSLINKED HYALURONAN POWDER AND METHOD FOR PRODUCING THE SAME

(75) Inventor: Tetsunori Matsumoto, Yokohama (JP)

(73) Assignee: Shiseido Company, Ltd., Chuo-ku, Tokyo ( * ) Notice: Subject to any disclaimer, the term of this patent is extended or adjusted under 35 U.S.C. 154(b) by 299 days.

(21) Appl. No.: 12/679,744

(22) PCT Filed: Sep. 26, 2008

(86) PCT No.: PCT/JP2008/067508
§ 371 (c)(1),
(2), (4) Date: Mar. 24, 2010

(87) PCT Pub. No.: WO2009/041627
PCT Pub. Date: Apr. 2, 2009

(65) Prior Publication Data
US 2010/0210587 A1    Aug. 19, 2010

(30) Foreign Application Priority Data
Sep. 28, 2007    (JP) ................................ 2007-253639

(51) Int. Cl.
*C07H 5/04*    (2006.01)
*C07H 5/06*    (2006.01)
*C08B 37/00*   (2006.01)

(52) U.S. Cl.
USPC ......... 536/18.7; 536/55.2; 536/55.3; 536/124

(58) Field of Classification Search
USPC ............................... 536/18.7, 55.2, 55.3, 124
See application file for complete search history.

(56) References Cited

U.S. PATENT DOCUMENTS

| 4,716,224 A | 12/1987 | Sakurai et al. |
| 7,674,781 B2 * | 3/2010 | Sheardown et al. ............ 514/54 |
| 2007/0026070 A1 * | 2/2007 | Vonwiller et al. ............ 424/486 |

FOREIGN PATENT DOCUMENTS

| GB | 2151244 | 7/1985 |
| GB | 2218429 | 11/1989 |
| JP | 7-102002 | 4/1995 |
| JP | 8-333402 | 12/1996 |
| JP | 2001-348401 | 12/2001 |
| WO | 97/04012 | 2/1997 |
| WO | 2006/056204 A1 | 6/2006 |

OTHER PUBLICATIONS

Extended European Search Report dated Jan. 26, 2011. Applicant—Shiseido Company Ltd.; Application 08832986.7-2115/2199308 (attached).
Japanese Abstract for Publication No. 08-333402 published Dec. 17, 1996, eight pages.
Japanese Abstract for Publication No. 07-102002 published Apr. 18, 1995, eight pages.
Japanese Abstract for Publication No. 2001-348401 published Dec. 18 2001, six pages.
International Preliminary Report on Patentability for corresponding PCT/JP2008/067508 mailed May 14, 2010, seven pages.
International Search Report for corresponding PCT/JP2008/067508 mailed Nov. 25, 2008, two pages.

* cited by examiner

*Primary Examiner* — Patrick Lewis
*Assistant Examiner* — Everett White
(74) *Attorney, Agent, or Firm* — Rankin, Hill & Clark LLP

(57) ABSTRACT

The present invention is provides a crosslinked hyaluronan powder excellent in swellability in water and a method for simply producing the same. A method for producing the swellable crosslinked hyaluronan powder is characterized by comprising mixing a crosslinking agent with a hyaluronan powder in a state dispersed in a liquid medium containing a monovalent alcohol having 1 to 4 carbon atoms and a solubility of the hyaluronan powder of less than 0.1 g/L to cause a crosslinking reaction. Also, the swellable crosslinked hyaluronan powder produced by the method has a swelling ratio in water of 500% or more.

11 Claims, 5 Drawing Sheets

Example 1

(a)

Example 5

(b)

Example 1

(a)

Example 5

(b)

(a)

(b)

(c)

(a)

(b)

SWELLABLE CROSSLINKED HYALURONAN POWDER AND METHOD FOR PRODUCING THE SAME

RELATED APPLICATIONS

The present invention relates to a swellable crosslinked hyaluronan powder and a method for producing the same, and in particular, relates to a crosslinked hyaluronan powder excellent in swellability and a method for simply producing the same.

FIELD OF THE INVENTION

A crosslinked hyaluronan gel in which a hyaluronan is crosslinked is excellent in biocompatibility and also has biodegradability, that is, in vivo degradation with the passage of time leading eventually to disappearance. Conventionally, it has been actively researched and developed to apply the crosslinked hyaluronan gel by utilizing such characteristics thereof to an adhesion preventing agent, a bone repairing agent, a controlled drug release composition, a tissue enlarging material, and so on. For example, a typical known example of the application to a tissue enlarging material is an anti-wrinkle injection in the field of cosmetic surgery.

BACKGROUND OF THE INVENTION

When the crosslinked hyaluronan gel is used as, for example, an anti-wrinkle injection, the crosslinked gel is required to have higher density and higher viscoelasticity for ensuring a certain volume in the injection portion. Also when the crosslinked hyaluronan gel is used as a controlled drug release preparation, in vivo retention for a long period of time is necessary for maintaining an adequate effect of the drug for a certain period of time. Therefore, a crosslinked hyaluronan gel having high density and high viscoelasticity is desirable.

Conventionally, the crosslinked hyaluronan gel has been prepared through a process including dissolving a solid hyaluronan in water, adding a crosslinking agent and an alkali thereto for a crosslinking reaction, and removing impurities (excess crosslinking agent and alkali) from the resulting hyaluronan gel (Patent Document 1).

However, since the hyaluronan has a high molecular weight, when it is dissolved in water, even if the concentration is low, the viscoelasticity of the aqueous solution is very high. Therefore, it takes significant time and effort to dissolve the hyaluronan in water in an industrial scale. In particular, when the concentration of a hyaluronan is increased for obtaining a crosslinked hyaluronan gel with high density, the viscosity of the liquid phase is significantly increased. Therefore, the processes of uniformly mixing the hyaluronan with a crosslinking agent and an alkali in an aqueous solution by stirring and of removing them by dialysis or the like are made very complicated. Thus, there has been a problem that large amounts of time and effort are necessary.

Furthermore, a crosslinked hyaluronan basically has high water swellability and viscoelasticity and thereby has problems that the handling thereof in storage, gel-preparation, or injection into a living body is difficult. Therefore, a crosslinked hyaluronan gel in a powder form that can be used as a desired gel by adding water at the point of use has been required. Furthermore, from the viewpoints of reducing the injection burden on a living body and allowing retention for a longer period of time in the living body, an approach to produce a crosslinked hyaluronan in a powder form and to directly inject the powder into a living body is also expected.

The crosslinked hyaluronan gel such as that disclosed in Patent Document 1 is produced by crosslinking a hyaluronan dissolved in water. Therefore, in order to obtain a crosslinked hyaluronan powder by such a conventional method, a crosslinked hyaluronan gel is produced, and then the gel is dried into a powder. However, the powder of the dried crosslinked hyaluronan gel released water without swelling, even if the water was added to the powder, and therefore the gel as that before being dried was not reproduced.

In addition, Patent Document 2 discloses a powder obtained by crosslinking a hyaluronan in a water-acetone liquid mixture, followed by heating for drying. However, the crosslinked hyaluronan powder obtained by this method is also poor in practical utility as a gel, because of its significantly low swellability in water to form approximately a viscous liquid state.

Patent Document 1: Japanese Patent No. 3094074
Patent Document 2: Japanese Unexamined Patent publication No. 60-130601

DISCLOSURE OF THE INVENTION

Problem to be Solved by the Invention

The present invention has been accomplished in view of the above-described conventional technology, and, in order to solve the problems, it is provided a crosslinked hyaluronan powder excellent in swellability in water and a method for simply producing the same.

Means to Solve the Problem

The present inventors have conducted intensive studies in view of the problems of the above-described conventional technology and, as a result, have found the fact that a swellable crosslinked hyaluronan powder can be easily produced by mixing a crosslinking agent with a hyaluronan powder in a state dispersed in a liquid medium containing a monovalent lower alcohol and not dissolving the hyaluronan powder to cause a crosslinking reaction and have found that the swellable crosslinked hyaluronan powder produced by this method swells remarkably in water to become a crosslinked hyaluronan gel excellent in viscoelasticity. Thus, the present invention has been accomplished.

That is, the swellable crosslinked hyaluronan powder according to the present invention has a swelling ratio in water of 500% or more.

In addition, the swellable crosslinked hyaluronan powder preferably has a concentration of the hyaluronan of 0.1 to 20% by weight when the powder is swollen with water to its utmost limit.

Furthermore, the method for producing the swellable crosslinked hyaluronan powder according to the present invention is characterized by comprising mixing a crosslinking agent with a hyaluronan powder in a state dispersed in a liquid medium that contains a monovalent alcohol having 1 to 4 carbon atoms and having a solubility of the hyaluronan powder of less than 0.1 g/L to cause a crosslinking reaction.

In the method for producing the swellable crosslinked hyaluronan powder, the liquid medium is preferably a solvent mixture of the monovalent alcohol and water.

In the method for producing the swellable crosslinked hyaluronan powder, the monovalent alcohol is preferably ethanol or 2-propanol.

In the method for producing the swellable crosslinked hyaluronan powder, the mixing ratio of the monovalent alcohol to water is preferably 99.9:0.1 to 65:35 as the mass ratio.

In the method for producing the swellable crosslinked hyaluronan powder, the water is preferably an alkaline buffer solution or an acidic buffer solution.

In the method for producing the swellable crosslinked hyaluronan powder, the crosslinking agent is preferably divinyl sulfone, 1,4-butanediol diglycidyl ether, and/or ethylene glycol diglycidyl ether.

Furthermore, the method for producing the swellable crosslinked hyaluronan powder according to the present invention is characterized by comprising the following steps (1) and (2):
(1) mixing a crosslinking agent with a hyaluronan powder in a state dispersed in a solvent containing a monovalent alcohol having 1 to 4 carbon atoms and an alkaline buffer solution and having a solubility of the hyaluronan powder of less than 0.1 g/L to cause a crosslinking reaction; and
(2) mixing a crosslinking agent with the product in the step (1) in a state dispersed in a solvent containing a monovalent alcohol having 1 to 4 carbon atoms and an acidic buffer solution and having a solubility of the hyaluronan powder of less than 0.1 g/L to cause a crosslinking reaction.

In the method for producing the swellable crosslinked hyaluronan powder, the mixing ratio of the monovalent alcohol to the alkaline buffer solution or the acidic buffer solution is preferably 99.9:0.1 to 65:35 as the mass ratio.

In the method for producing the swellable crosslinked hyaluronan powder, the crosslinking agent is preferably divinyl sulfone, 1,4-butanediol diglycidyl ether, and/or ethylene glycol diglycidyl ether.

Effect of the Invention

According to the present invention, a swellable crosslinked hyaluronan powder can be easily obtained by performing a crosslinking reaction in a state in which a hyaluronan powder is dispersed, without passing through complicated processes performed in conventional methods. Therefore, it is very useful from the standpoints of time and cost. In addition, the swellable crosslinked hyaluronan powder obtained by the present invention has high water swellability when the powder is swollen with water and excellent viscoelasticity.

BEST MODE FOR CARRYING OUT THE INVENTION

Figure 1:
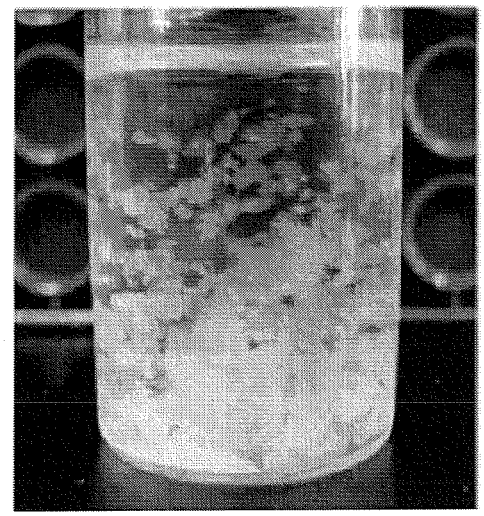
FIG. 1 includes photographic views of crosslinked hyaluronan powders prepared in Examples 1 and 5 of the present invention in the state that they are swollen with an excess amount of purified water ((a): Example 1, (b): Example 5).
Figure 1:
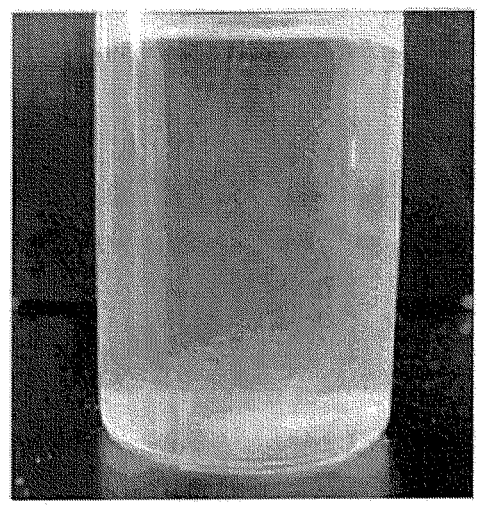

The swellable crosslinked hyaluronan powder according to the present invention has a swelling ratio in water of 500% or more.

Here, the term "a swelling ratio of 500% or more" refers to that when a certain amount of the swellable crosslinked hyaluronan powder is swollen with a large excess amount of pure water into a crosslinked hyaluronan gel, the weight of the swollen crosslinked hyaluronan gel is 500% or more, provided that the weight of the crosslinked hyaluronan powder is 100%, that is, the powder swells 5 times or more.

Furthermore, the concentration of the hyaluronan when the swellable crosslinked hyaluronan powder is maximumly swollen with water is 0.1 to 20% by weight. Therefore, the swellable crosslinked hyaluronan powder according to the present invention preferably has a swelling ratio of 500 to 100,000%.

The swellable crosslinked hyaluronan powder according to the present invention can be applied to a medicine, a cosmetic, or the like directly or by being blended in an appropriate formulation. Furthermore, in particular, the crosslinked hyaluronan powder according to the present invention can be re-swollen from the state of a powder and, therefore, can be suitably applied to a material used in vivo, for example, a tissue enlarging material such as an anti-wrinkle injection, a controlled drug release composition, an adhesion preventing agent, or a bone repairing agent.

In addition, the swellable crosslinked hyaluronan powder according to the present invention may be swollen in water and then be applied to the above-mentioned purposes as a crosslinked hyaluronan gel.

In addition, in the method for producing the swellable crosslinked hyaluronan powder according to the present invention, the hyaluronan powder in the state dispersed in a liquid medium containing a monovalent alcohol having 1 to 4 carbon atoms and not dissolving the hyaluronan powder is mixed with a crosslinking agent for conducting a crosslinking reaction.

The hyaluronan powder used in the production method of the present invention is a straight-chain polymer in which N-acetyl-D-glucosamine residues and D-glucuronic acid residues are alternately coupled to each other as shown in the following formula, and the straight-chain polymer can be used without particular limitation as long as it is in a powder form.

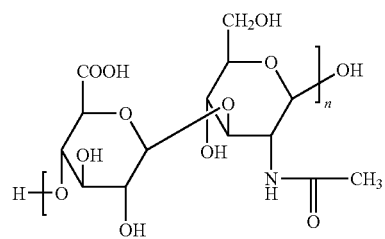

The hyaluronan can be obtained by, for example, extraction and isolation from a cockscomb or other animal tissues or fermentation using microorganisms such as *Streptococcus*. In addition, in the present invention, a powder of a hyaluronan derivative, for example, a metal salt of a hyaluronan such as a sodium salt of a hyaluronan or a potassium salt of a hyaluronan or a hyaluronan derivative in which the hydroxyl group, the carboxyl group, or another group of a hyaluronan is etherified, esterified, amidated, acetalized, or ketalized may be used.

Furthermore, the hyaluronan powder may be a commercially available one.

Examples of the commercially available hyaluronan include Biohyalo 12 (manufactured by Shiseido Co., Ltd.) and hyaluronan (manufactured by Kibun Foods, Inc.).

The molecular weight of the hyaluronan powder used in the production method of the present invention is not particularly limited, but is preferably 100000 or more and further preferably about 500000 to 3000000. Usually, the molecular weights of almost all of the hyaluronans generally used are 100000 or more, but some hyaluronans have a particularly lowered molecular weight of about 10000. If such a hyaluronan having a lowered molecular weight of about 10000 is used in the present invention, a crosslinked hyaluronan gel having desired viscoelasticity may not be obtained when the swellable crosslinked hyaluronan powder is swollen with water. Therefore, such a hyaluronan is not so desirable.

Furthermore, when a hyaluronan powder is dissolved in a liquid medium, the resulting solution is a viscous transparent liquid. On the other hand, when a hyaluronan powder is dispersed in a liquid medium not to be dissolved therein, the presence of dispersing particles of the hyaluronan powder is observed in the liquid medium. Furthermore, in the production method of the present invention, since the hyaluronan powder dispersed, without being dissolved, in a liquid medium in the powder form is subjected to a crosslinking reaction, no increase in the viscosity of the liquid phase occurs, and even a dispersion containing the hyaluronan in a high concentration can be easily treated. In the production method of the present invention, the concentration of the hyaluronan powder for the crosslinking reaction is not particularly limited as long as the crosslinking reaction is not impaired. It is possible to treat the hyaluronan in a high concentration of about 50 W/V %, but the concentration is preferably 0.1 to 30 W/V % and further preferably 1 to 20 W/V % in the mixture for the crosslinking reaction.

The liquid medium used in the production method of the present invention contains a monovalent alcohol having 1 to 4 carbon atoms and does not dissolve the hyaluronan powder.

The monovalent alcohol having 1 to 4 carbon atoms includes, but not be limited to, methanol, ethanol, 1-propanol, 2-propanol, 1-butanol, 2-methyl-1-propanol, 2-butanol, and 2-methyl-2-propanol. Among them, methanol, ethanol, 1-propanol, and 2-propanol can be particularly preferably used. In the present invention, the use of ethanol or 2-propanol is particularly preferred.

Incidentally, in the production method of the present invention, for example, when a polyvalent alcohol such as ethylene glycol is used, the medium dissolves the hyaluronan powder, and when a ketone such as acetone is used, the swelling ratio of the resulting crosslinked hyaluronan powder in water may be less than 500% not to provide a desired crosslinked hyaluronan gel.

In the present invention, the term "not dissolving hyaluronan powder" specifically refers to that the solubility of the hyaluronan powder is less than 0.1 g/L (25° C.).

Examples of the liquid medium used in the production method of the present invention include a solvent mixture of the above-mentioned monovalent alcohol and water. Here, if the blended ratio of water in the solvent mixture is too high, the liquid medium dissolves the hyaluronan powder to increase the viscosity of the liquid phase, resulting in an increase in difficulty of handling. This makes it difficult to produce a swellable crosslinked hyaluronan powder. Therefore, the mass ratio of the monovalent alcohol to water (monovalent alcohol:water) in the solvent mixture is preferably 99.9:0.1 to 65:35. Furthermore, the mass ratio (monovalent alcohol:water) is more preferably 99.9:0.1 to 85:15.

The crosslinking agent used in the production method of the present invention may be any agent that can crosslink between the polymer chains of the hyaluronan by chemical bonds. As the crosslinking agent of the hyaluronan, polyfunctional compounds having two or more functional groups that form covalent bonds by reacting with reactive functional groups of the hyaluronan molecule, such as a carboxyl group, a hydroxyl group, or an acetamide group, can be used. Examples of the crosslinking agent used in the present invention include alkyl diepoxy compounds such as 1,3-butadiene diepoxide, 1,2,7,8-diepoxyoctane, and 1,5-hexadiene diepoxide; diglycidyl ether compounds such as ethylene glycol diglycidyl ether, 1,4-butanediol diglycidyl ether, and bisphenol A diglycidyl ether; divinyl sulfone; and epichlorohydrin. Among them, in particular, divinyl sulfone, 1,4-butanediol diglycidyl ether, and ethylene glycol diglycidyl ether can be preferably used. Furthermore, in the present invention, an arbitrary combination of two or more crosslinking agents may be used.

In addition, in the production method of the present invention, the blended amount of the crosslinking agent is not particularly limited, but, specifically, is preferably 0.1 to 10 W/V % and more preferably 0.5 to 5 W/V % in the mixture for the crosslinking reaction.

Furthermore, in the production method of the present invention, in order to enhance the reactivity of the hyaluronan during the crosslinking reaction, the pH of the mixture may be suitably adjusted by adding an acid such as hydrochloric acid or sulfuric acid, a base such as sodium hydroxide or potassium hydroxide, or an appropriate buffer solution such as phosphate or quaternary ammonium to the mixture for the crosslinking reaction, or the crosslinking reaction may be performed under alkaline or acidic conditions.

For example, if the crosslinking reaction is performed under alkaline conditions by using a 0.001 to 0.1 N alkaline buffer solution instead of water of the liquid medium, the hydroxymethyl group of the hyaluronan molecule forms an ether bond with the crosslinking agent to achieve the crosslinking.

Furthermore, if the crosslinking reaction is performed under acidic conditions by using a 0.001 to 0.1 N acidic buffer solution instead of water of the liquid medium, the carboxyl group of the hyaluronan molecule forms an ester bond with the crosslinking agent to achieve the crosslinking.

In a swellable crosslinked hyaluronan powder prepared by the crosslinking reaction under alkaline or acidic conditions, the swelling ratio when the powder is swollen with water is further higher than that of a powder prepared by using water as the liquid medium, and the crosslinked hyaluronan gel provided is excellent in viscoelasticity. In addition, the viscoelasticity of the crosslinked hyaluronan gel also varies depending on the concentration of each buffer solution, and, in general, there is a tendency that the loss elastic modulus decreases with an increase in alkali concentration to provide a gel with a high shape retention property. Therefore, in the production of the swellable crosslinked hyaluronan powder according to the present invention, a crosslinked hyaluronan gel of which swellability and viscoelasticity comply with the application or purpose can be obtained by controlling the alkaline or acidic condition during the crosslinking reaction.

Furthermore, in the production method of the present invention, in addition to the above-mentioned essential components, components that are usually used in a medicine or a cosmetic may be added to the mixture for, the crosslinking reaction in advance within the range that does not affect the purposes and effects of the present invention. Examples of the components that may be added include moisturizing agents, such as ascorbic acid and derivatives thereof and glycerin, and anti-inflammatory agents, such as retinol and derivatives thereof and salicylic acid.

In the production method of the present invention, the reaction time for the crosslinking reaction varies depending on, for example, the blended amounts of the hyaluronan powder as the raw material and the crosslinking agent and also physical properties of the objective crosslinked hyaluronan powder, and is usually from 30 minutes to 100 hours and more preferably from 1 hour to 72 hours.

Furthermore, in the production method of the present invention, the crosslinking reaction may be performed under heating for shortening the reaction time by accelerating the reaction. The reaction temperature can be set from 20 to 120° C., but is more preferably from 25 to 90° C. Furthermore, after the crosslinking reaction, a crosslinked hyaluronan gel in a powder form can be obtained by conducting solid-liquid separation by a known method such as centrifugation or filtration and then washing and drying the resulting powder by an ordinary method.

Furthermore, in the production method of the present invention, the physical properties, such as swelling ratio in water and viscoelasticity, of the resulting swellable crosslinked hyaluronan powder can be changed by varying the reaction temperature, the reaction time, the types and the concentrations of the hyaluronan powder and the crosslinking agent used, and so on. Therefore, these conditions may be appropriately determined according to the physical properties of the objective swellable crosslinked hyaluronan powder.

Furthermore, the production method according to the present invention includes a method of producing a swellable double crosslinked hyaluronan powder, as another embodiment.

Herein, the term "double crosslinked" refers to that both the hydroxy group and the carboxyl group of a hyaluronan molecule are applied to the crosslinking reaction with a crosslinking agent.

In the present invention, the swellable double crosslinked hyaluronan powder can be produced through the following steps (1) and (2):
(1) mixing a crosslinking agent with a hyaluronan powder in a state dispersed in a solvent containing a monovalent alcohol having 1 to 4 carbon atoms and an alkaline buffer solution and having a solubility of the hyaluronan powder of less than 0.1 g/L to cause a crosslinking reaction; and
(2) mixing a crosslinking agent with the product in the step (1) in a state dispersed in a solvent containing a monovalent alcohol having 1 to 4 carbon atoms and an acidic buffer solution and having a solubility of the hyaluronan powder of less than 0.1 g/L to cause a crosslinking reaction.

The step (1) indicates that the crosslinking reaction is performed under alkaline conditions to form ether crosslinking in the hyaluronan molecule, and the step (2) indicates that the crosslinking reaction is performed under acidic conditions to form ester crosslinking in the hyaluronan molecule.

Therefore, in the steps (1) and (2), for example, the hyaluronan powder, the solvent, and the composition relating to the crosslinking reaction can conform to those described above.

The crosslinking agents in both the steps (1) and (2) are preferably the same, and a diglycidyl ether such as divinyl sulfone, 1,4-butanediol diglycidyl ether, or ethylene glycol diglycidyl ether can be preferably used.

A method for producing swellable double crosslinked hyaluronan powder will be exemplarily shown below, but is merely an example and does not limit the present invention.
(Production Example of Swellable Crosslinked Hyaluronan Powder)

A crosslinking agent is mixed with a liquid solvent prepared by mixing a monovalent alcohol having 1 to 4 carbon atoms and a 0.01 to 0.1 N sodium hydroxide aqueous solution at a mass ratio of 99.9:0.1 to 65:35. Then, a hyaluronan powder is added thereto for dispersion, followed by a crosslinking reaction under appropriate conditions. After the crosslinking reaction, the hyaluronan powder is collected by centrifugation, filtration, or the like and is washed and dried by an ordinary method to give a swellable crosslinked hyaluronan powder.

Then, the swellable crosslinked hyaluronan powder is added to a liquid mixture of a crosslinking agent and a liquid solvent prepared by mixing a monovalent alcohol having 1 to 4 carbon atoms and a 0.01 to 0.1 N hydrochloric acid aqueous solution at a mass ratio of 99.9:0.1 to 65:35 for dispersion, and a crosslinking reaction under appropriate conditions is performed again. After the crosslinking reaction, similarly, the hyaluronan powder is collected by filtration and is washed and dried to give a swellable double crosslinked hyaluronan powder.

The shape retention property of the crosslinked hyaluronan gel swollen with water tends to be increased by the double crosslinking, compared to that in the case that the crosslinking is performed under either the alkaline or acidic conditions. In addition, the viscoelasticity of the gel can be adjusted by controlling the concentration of the alkaline and acidic buffer solution, and, in general, a higher alkali concentration gives a gel with higher elasticity.

Such a swellable double crosslinked hyaluronan powder and a gel derived from the powder exhibit physical properties that are similar to so-called elasticity of skin, and are therefore particularly suitable to be used as tissue enlarging material such as anti-wrinkle injection.

Incidentally, when the crosslinking reaction under alkaline conditions is performed after the crosslinking reaction under acidic conditions, there is a tendency that the ester crosslinking previously formed is hydrolyzed by the exposure to the alkaline conditions, and, at the same time, the formation of ether crosslinking on the hydroxy group is prevented. The thus obtained crosslinked hyaluronan powder and the gel derived from the powder are low in swellability and viscoelasticity and are therefore inadequate to be used as tissue enlarging material, but, on the other hand, are expected to be used as a moisturizing agent for cosmetics.

Since a conventional method for producing a crosslinked hyaluronan gel uses water as the liquid medium, the viscosity is very high even if the concentration of the hyaluronan aqueous solution is low.

On the other hand, in the method of the present invention, since the hyaluronan powder is dispersed in a liquid medium while maintaining the powder form without being dissolved, an increase in the viscosity of the liquid phase does not occur. Therefore, the dispersion can be easily stirred and mixed with a magnet stirrer, a stirring rod, a shaker, or the like. In addition, since an increase in viscosity of the liquid phase does not occur during the reaction also, it is possible to treat a hyaluronan dispersion in a very high concentration.

Furthermore, according to the production method of the present invention, the step of dissolving hyaluronan in water, which takes very long time conventionally, is unnecessary. In addition, since the generated crosslinked hyaluronan can be readily separated by, for example, centrifugation or filtration, the steps for removing the crosslinking agent, acid, alkali, and so on can be significantly simplified compared to those in the conventional method. Therefore, according to the production method of the present invention, it is possible to very easily produce crosslinked hyaluronan, compared to the conventional method using a hyaluronan aqueous solution, and thereby the manufacturing time and cost can be significantly reduced.

Furthermore, in the conventional production method, the crosslinked hyaluronan is obtained as a gel containing water. When the crosslinked hyaluronan powder obtained by drying the gel by a known method is put in water again, the powder releases the water or is dissolved in the water without being re-swollen.

On the other hand, the swellable crosslinked hyaluronan powder obtained by the method of the present invention has a significantly high swelling ratio in water of 500% or more. That is, according to the present invention, a "swellable" crosslinked hyaluronan powder, which has been conventionally impossible to be achieved, can be obtained.

EXAMPLES

The present invention will now be described further in detail with reference to specific examples, but is not limited to these examples.

The present inventors have tried first to prepare a swellable crosslinked hyaluronan powder by mixing a crosslinking agent with a hyaluronan powder in the state of being dispersed in a monovalent lower alcohol/water solvent mixture.

Examples 1 and 2

A hyaluronan powder (Biohyalo 12, molecular weight: 1200000, manufactured by Shiseido Co., Ltd.) was added and dispersed so as to give a concentration of 3.3 W/V % in a reaction solution prepared by mixing 10 parts of a 0.1 N sodium hydroxide aqueous solution, 87 parts of ethanol, and 3 parts of a crosslinking agent (ethylene glycol diglycidyl ether: Denacol EX-810P, manufactured by Nagase Chemicals Co., Ltd.) for conducting a crosslinking reaction at room temperature (Example 1) or at 45° C. (Example 2) for 16 hours. After the completion of the reaction, the hyaluronan powders were collected by filtration and then washed with ethanol and dried. The resulting crosslinked hyaluronan powders were swollen with an excess amount of purified water to give clear and colorless to white crosslinked hyaluronan gels in both the room temperature conditions (Example 1) and the heating conditions at 45° C. (Example 2). On this occasion, the swelling ratio (by weight) of each crosslinked hyaluronan powder was 500% or more.

FIG. 1(a) shows a photographic view of the crosslinked hyaluronan powder, in the state of being swollen with an excess amount of purified water, prepared under room temperature conditions in Example 1, and FIG. 2(a) is a photographic view of that in the state of being dried. The size of the crosslinked hyaluronan gel in the swollen state was about 2 to 7 mm.

Example 3

It was tried to prepare a crosslinked hyaluronan powder as in the above Examples 1 and 2 under room temperature conditions except that 3 parts of divinyl sulfone was used as the crosslinking agent instead of the 3 parts of ethylene glycol diglycidyl ether. The resulting crosslinked hyaluronan powder was swollen with an excess amount of purified water to give a clear and colorless to white crosslinked hyaluronan gel. The size of the crosslinked hyaluronan gel was about 1 to 5 mm. In addition, the swelling ratio (by weight) of the crosslinked hyaluronan powder was 500% or more.

Example 4

It was tried to prepare a crosslinked hyaluronan powder as in the above Examples 1 and 2 under room temperature conditions except that 3 parts of 1,4-butanediol diglycidyl ether was used as the crosslinking agent instead of the 3 parts of ethylene glycol diglycidyl ether. The resulting crosslinked hyaluronan powder was swollen with an excess amount of purified water to give a clear and colorless to white crosslinked hyaluronan gel. The size of the crosslinked hyaluronan gel was about 2 to 8 mm. Furthermore, the swelling ratio (by weight) of the crosslinked hyaluronan powder was 500% or more.

Examples 5 and 6

It was tried to prepare crosslinked hyaluronan powders as in the above Examples 1 and 2 except that 10 parts of purified water was used instead of the 10 parts of a 0.1 N sodium hydroxide aqueous solution. The resulting crosslinked hyaluronan powders were swollen with an excess amount of purified water to give clear and colorless to white crosslinked hyaluronan gels in both the room temperature conditions (Example 5) and the heating conditions at 45° C. (Example 6). On this occasion, the swelling ratio (by weight) of each crosslinked hyaluronan powder was 500% or more.

FIG. 1(b) shows a photographic view of the crosslinked hyaluronan powder, in the state of being swollen with an excess amount of purified water, prepared under room temperature conditions in Example 5, and FIG. 2(b) is a photographic view of that in the state of being dried. The size of the crosslinked hyaluronan gel in the swollen state was about 0.1 to 0.5 mm.

The raw materials used in the above Examples 1 to 6, the reaction conditions, and the results thereof are tabulated in the following Table 1.

TABLE 1

| | Examples | | | | | |
|---|---|---|---|---|---|---|
| | 1 | 2 | 3 | 4 | 5 | 6 |
| Hyaluronic acid | 3.3 | 3.3 | 3.3 | 3.3 | 3.3 | 3.3 |
| 0.1N sodium hydroxide aqueous solution | 10 | 10 | 10 | 10 | — | — |
| Purified water | — | — | — | — | 10 | 10 |
| Ethanol | 87 | 87 | 87 | 87 | 87 | 87 |
| Ethylene glycol diglycidyl ether | 3 | 3 | — | — | 3 | 3 |
| Divinyl sulfone | — | — | 3 | — | — | — |
| 1,4-butanediol diglycidyl ether | — | — | — | 3 | — | — |
| Reaction temperature | RT | 45° C. | RT | RT | RT | 45° C. |
| Production of crosslinked hyaluronic acid gel (swelling ratio of 500% or more) | ○ | ○ | ○ | ○ | ○ | ○ |

It has been made obvious from the above Examples 1 to 6 that a swellable crosslinked hyaluronan powder having a swelling ratio in water of 500% can be obtained by using an ethanol/water solvent mixture (ethanol: water=10.3:89.7) and conducting a crosslinking reaction in the state in which a hyaluronan powder is dispersed in the solvent mixture under room temperature conditions, heating conditions at 45° C., and using each of the crosslinking agents.

Furthermore, in the above Examples 1 to 6, since the hyaluronan powder was not dissolved in the liquid medium during the crosslinking reaction, an increase in viscosity of the liquid phase did not occur, treatment such as stirring was very easy, and also the product could be easily separated by filtration.

Figure 2:
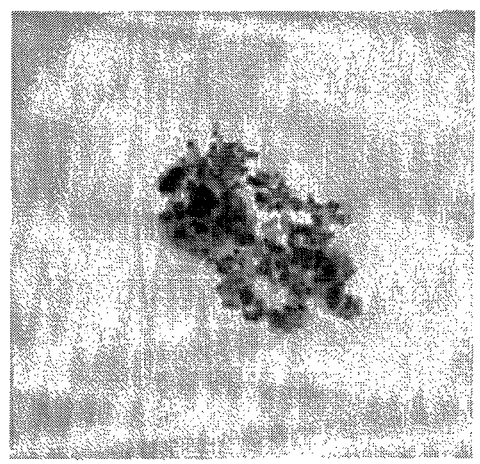
FIG. 2 includes photographic views of crosslinked hyaluronan powders prepared in Examples 1 and 5 of the present invention in the dried state thereof ((a): Example 1, (b): Example 5).
Figure 2:
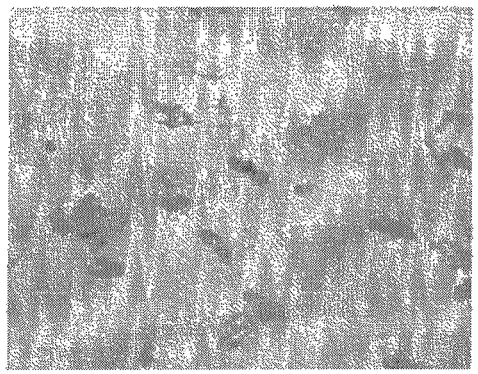

Furthermore, it was confirmed, from FIGS. 1 and 2 that the powder of Example 1, in which an alkali was added, could provide a gel of particles with a large size by further developed crosslinking reaction (FIGS. 1(a) and 2(a)). On the other hand, the powder of Example 5, in which an alkali was not added, provided a crosslinked hyaluronan gel of fine particles. Since each of these particles was swollen with pure water, it was confirmed that crosslinking was formed inside the particle (FIGS. 1(b) and 2(b)). In addition, the concentration of the hyaluronan when this crosslinked hyaluronan powder was maximumly swollen in water was in the range of 0.1 to 20% by weight, and it has been made obvious that a crosslinked hyaluronan gel excellent in swellability and viscoelasticity could be obtained.

Examples 7 and 8

It was tried to prepare crosslinked hyaluronan gels as in the above Examples 1 and 2 except that 87 parts of isopropanol was used instead of the 87 parts of ethanol. The resulting crosslinked hyaluronan powders were swollen with an excess amount of purified water to give clear and colorless to white crosslinked hyaluronan gels in both the room temperature conditions (Example 7) and the heating conditions at 45° C. (Example 8). On this occasion, the swelling ratio (by weight) of each crosslinked hyaluronan powder was 500% or more.

Examples 9 and 10

It was tried to prepare crosslinked hyaluronan gels as in the above Examples 5 and 6 except that 87 parts of isopropanol was used instead of the 87 parts of ethanol. The resulting crosslinked hyaluronan powders were swollen with an excess amount of purified water to give clear and colorless to white crosslinked hyaluronan gels in both the room temperature conditions (Example 9) and the heating conditions at 45° C. (Example 10). On this occasion, the swelling ratio (by weight) of each crosslinked hyaluronan powder was 500% or more.

Comparative Example 1

It was tried to prepare a crosslinked hyaluronan gel as in the above Example 2 except that 87 parts of ethylene glycol was used instead of the 87 parts of ethanol. As a result, the hyaluronan powder was dissolved in the solvent mixture to make the mixing by stirring impossible. Therefore, the treatment was terminated.

Comparative Example 2

It was tried to prepare a crosslinked hyaluronan gel as in the above Example 2 except that 87 parts of acetone was used instead of the 87 parts of ethanol. The resulting crosslinked hyaluronan powder was swollen with an excess amount of purified water, which colored the dispersion medium yellow to suggest that the hyaluronan was degraded. Therefore, the treatment was terminated. In addition, the crosslinked hyaluronan powder in water released the water, and the swelling ratio (by weight) was less than 500%.

The raw materials used in the above Examples 7 to 10 and Comparative Examples 1 and 2, the reaction conditions, and the results thereof are tabulated in the following Table 2.

TABLE 2

|  | Examples | | | | Comparative Examples | |
| --- | --- | --- | --- | --- | --- | --- |
|  | 7 | 8 | 9 | 10 | 1 | 2 |
| Hyaluronic acid | 3.3 | 3.3 | 3.3 | 3.3 | 3.3 | 3.3 |
| 0.1N sodium hydroxide aqueous solution | 10 | 10 | — | — | 10 | 10 |
| Purified water | — | — | 10 | 10 | — | — |
| Isopropanol | 87 | 87 | 87 | 87 | — | — |
| Ethylene glycol | — | — | — | — | 87 | — |
| Acetone | — | — | — | — | — | 87 |
| Crosslinking agent | 3 | 3 | 3 | 3 | 3 | 3 |
| Reaction temperature | RT | 45° C. | RT | 45° C. | 45° C. | 45° C. |
| Production of crosslinked hyaluronic acid gel (swelling ratio of 500% or more) | ○ | ○ | ○ | ○ | X | X |

It has been made obvious from the above Examples 7 to 10 that a swellable crosslinked hyaluronan powder having a swelling ratio in water of 500% can be obtained by using an isopropanol/water solvent mixture (isopropanol: water=10.3: 89.7) in both the room temperature conditions and the heating conditions at 45° C., as in Examples 1 to 4 in which the ethanol/water solvent mixture was used.

On the other hand, as in the above Comparative Example 1, when a solvent mixture of ethylene glycol/water, which is polyvalent alcohol, and water was used, the hyaluronan powder was dissolved therein, which made the mixing by stirring difficult. Therefore, the crosslinked hyaluronan gel was not easily produced. In addition, as in the above Comparative Example 2, when a solvent mixture of acetone/water was used, though the hyaluronan powder was not dissolved during the production process, the dispersion medium was colored yellow. Therefore, a crosslinked hyaluronan powder with high quality was not obtained. In addition, the powder in Comparative Example 2 was hardly swollen in water and was inferior to those in Examples 7 to 10 also in the swelling ratio.

Then, the present inventors have tried to prepare a swellable crosslinked hyaluronan powder as in the above Example 2 by arbitrarily changing the mass ratio of ethanol to water for investigating the mixture ratio of a monovalent lower alcohol to water.

Example 11

It was tried to prepare a crosslinked hyaluronan powder as in the above Example 2 except that 20 parts of purified water and 77 parts of ethanol were used. The resulting crosslinked hyaluronan powder was swollen with an excess amount of purified water to give a clear and colorless to white crosslinked hyaluronan gel having a swelling ratio of 500% or more with respect to the powder.

Example 12

It was tried to prepare a crosslinked hyaluronan powder as in the above Example 2 except that 30 parts of purified water and 67 parts of ethanol were used. The resulting crosslinked hyaluronan powder was swollen with an excess amount of purified water to give a clear and colorless to white crosslinked hyaluronan gel having a swelling ratio of 500% or more with respect to the powder.

Comparative Example 3

It was tried to prepare a crosslinked hyaluronan powder as in the above Example 2 except that 40 parts of purified water and 57 parts of ethanol were used. As a result, the hyaluronan powder was dissolved in the solvent mixture to make the mixing by stirring impossible. Therefore, the treatment was terminated.

The raw materials used in the above Examples 11 to 12 and Comparative Example 3, the reaction conditions, and the results thereof are tabulated in the following Table 3.

TABLE 3

|  | Examples | | | Comparative |
| --- | --- | --- | --- | --- |
|  | 2 | 11 | 12 | Example 3 |
| Hyaluronic acid | 3.3 | 3.3 | 3.3 | 3.3 |
| Purified water | 10 | 20 | 30 | 40 |
| Ethanol | 87 | 77 | 67 | 57 |
| Crosslinking agent | 3 | 3 | 3 | 3 |
| Ethanol:Water (mass ratio) | 89.7:10.3 | 79.4:20.6 | 69.1:30.9 | 58.8:41.2 |
| Reaction temperature | RT | RT | RT | RT |
| Production of crosslinked hyaluronic acid gel (swelling ratio of 500% or more) | ○ | ○ | ○ | ○ |

It has been made obvious from Table 3 above that when a solvent mixture of ethanol/water in a mass ratio of about 90:10 to 70:30 is used, the solubility of the hyaluronan in the solvent is 0.1 g/L to give a swellable crosslinked hyaluronan in a powder form. In addition, it was confirmed that the particle sizes of the crosslinked hyaluronan gels prepared by swelling the above-mentioned powders with water were increased with the ratio of water (Example 2<Example 11<Example 12).

However, as shown by Comparative Example 3, the viscosity of the liquid phase was increased when the ratio of water exceeds 40% to make the mixing by stirring difficult. Therefore, a crosslinked hyaluronan powder could not be produced.

The present inventors have further investigated and, as a result, have confirmed that the hyaluronan powder is not dissolved in a solvent mixture until the mass ratio of the monovalent alcohol to water (monovalent alcohol:water) reaches about 65:35 and that the swellable crosslinked hyaluronan powder can be easily produced.

The present inventors compared the crosslinked hyaluronan gels prepared from the powders in Comparative Example 4 to 6 described below with that prepared in the above Example 2 for investigating the swellability of the crosslinked hyaluronans in powder forms prepared by different methods. The results are shown in the following Table 4.

Comparative Example 4

A commercially available crosslinked hyaluronan gel (Restylane, manufactured by Q-Med AB, Sweden) was lyophilized into a powder form. The resulting powder was put in an excess amount of purified water for re-swelling. The powder released the water and did not give a crosslinked hyaluronan gel as that of the original.

Comparative Example 5

A commercially available crosslinked hyaluronan gel (Hylaform, manufactured by Genzyme Corp. USA) was lyophilized into a powder form. The resulting powder was put in an excess amount of purified water for re-swelling. The powder released water and did not give a crosslinked hyaluronan gel as that of the original.

Comparative Example 6

The crosslinked hyaluronan powder prepared in Example 2 was swollen with an excess amount of purified water to give a crosslinked hyaluronan gel. The gel was lyophilized into a powder form. The resulting powder was put in an excess amount of purified water for re-swelling. The powder released the water and did not give a crosslinked hyaluronan gel as that of the original.

TABLE 4

|  | Example 2 | Comparative Example 4 | Comparative Example 5 | Comparative Example 6 |
| --- | --- | --- | --- | --- |
| Production of crosslinked hyaluronic acid gel (swelling ratio of 500% or more) | ○ | X | X | X |

As shown in Table 4 above, it is obvious that a crosslinked hyaluronan gel could not be given by re-swelling the powder obtained by drying a crosslinked hyaluronan gel. Therefore, the production method according to the present invention is suitable for providing a "swellable" crosslinked hyaluronan "powder" having a swelling ratio of 500% or more.

Figure 3:
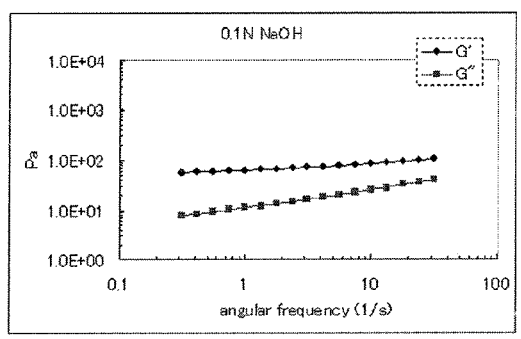
FIG. 3 includes graphs comparing dynamic viscoelasticity of the crosslinked hyaluronan gel prepared in Example 13 of the present invention and the hyaluronan gels obtained from commercially available crosslinked hyaluronan gels produced by conventional methods ((a): Example 13, (b): Comparative Example 7, (c): Comparative Example 8).
Figure 3:
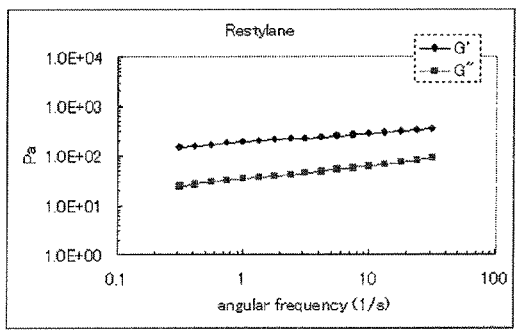
Figure 3:
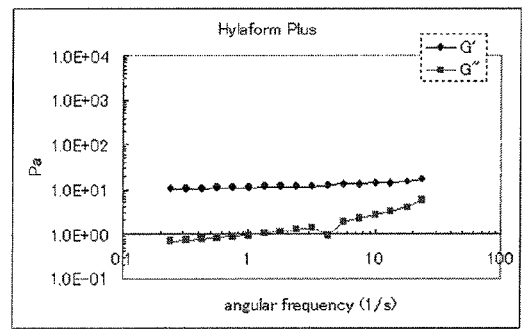

The crosslinked hyaluronan gels shown in the following Examples and Comparative Examples were evaluated for dynamic viscoelasticity. The results are shown in FIG. 3 (FIG. 3(a): Example 13, (b): Comparative Example 7, (c): Comparative Example 8).

(Measurement of Dynamic Viscoelasticity)

The storage elastic modulus G' (Pa) and the loss elastic modulus G" (Pa) were measured within the angular frequency range of 0.1 to 100 (1/sec) with a stress-controlled rheometer (AR1000—N) manufactured by TA Instruments.

Example 13

A hyaluronan powder (Biohyalo 12, molecular weight: 1200000, manufactured by Shiseido Co., Ltd.) was added and dispersed to give a concentration of 3.3 W/V % in 10 parts of a 0.1 N sodium hydroxide aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the hyaluronan powder was collected by filtration and then washed with ethanol and dried to give a swellable crosslinked hyaluronan powder. The powder was added in a physiological saline in a concentration of 2% by weight for swelling. The resulting crosslinked hyaluronan gel was used for viscoelasticity measurement.

Comparative Example 7

A commercially available crosslinked hyaluronan gel (Restylane, manufactured by Q-Med AB, Sweden) was used for viscoelasticity measurement.

Comparative Example 8

A commercially available hyaluronan preparation (Hylaform, manufactured by Genzyme Corp. USA) was used for viscoelasticity measurement.

As shown in FIG. 3, the crosslinked hyaluronan gel (Example 13) produced by the method according to the present invention has excellent viscoelasticity that is intermediately positioned between commercially available crosslinked hyaluronan gels (Comparative Examples 7 and 8) that are used as anti-wrinkle injections.

It is suggested that the crosslinked hyaluronan gels of Comparative Examples 7 and 8 are obtained by a crosslinking reaction in a hyaluronan aqueous solution and are directly formed without through a powder form.

From the results above, it has been made obvious that the swellable crosslinked hyaluronan powder produced by the method according to the present invention can swell to become a gel having excellent viscoelasticity that can be used as a tissue enlarging material. The powder exhibits excellent elasticity not depending on each frequency and is therefore thought to be suitable, in particular, as an anti-wrinkle injection.

Figure 4:
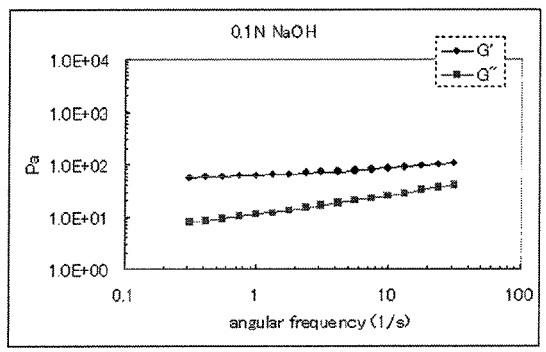
FIG. 4 includes graphs comparing dynamic viscoelasticity of the crosslinked hyaluronan gels prepared in Examples 13 and 14 of the present invention ((a): Example 13, (b): Example 14).
Figure 4:
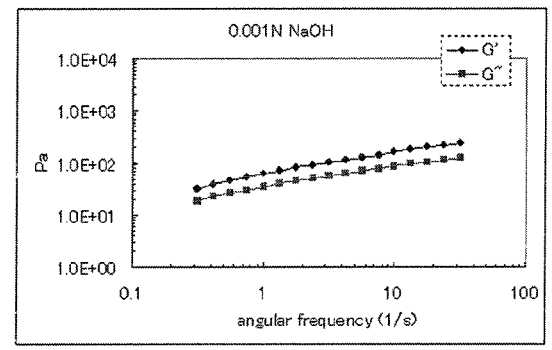

Then, the crosslinked hyaluronan gels shown in the above-described Example 13 and the below-described Example 14 were measured for dynamic viscoelasticity for comparing the characteristics. The results are shown in FIG. 4 (FIG. 4(a): Example 13, (b): Example 14). Incidentally, the dynamic viscoelasticity was measured according to the above-mentioned method.

Example 14

A hyaluronan powder (Biohyalo 12, molecular weight: 1200000, manufactured by Shiseido Co., Ltd.) was added and dispersed to give a concentration of 3.3 W/V % in 10 parts of a 0.001 N sodium hydroxide aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the hyaluronan powder was collected by filtration and then washed with ethanol and dried to give a swellable crosslinked hyaluronan powder. The powder was added in a physiological saline in a concentration of 2% by weight for swelling. The resulting crosslinked hyaluronan gel was used for viscoelasticity measurement.

As shown in FIG. 4, both the crosslinked hyaluronan gels of Examples 13 and 14 prepared from the swellable crosslinked hyaluronan powders according to the present invention exhibited excellent viscoelasticity. In particular, the frequency dependency in storage elastic modulus (G') and the loss elastic modulus (G") of the gel of Example 13 in which the alkali concentration in the production system was high were lower than those of the gel of Example 14.

From the above, it has been made obvious that the swellable crosslinked hyaluronan powder produced by using a liquid medium containing a 0.001 to 0.1 N alkaline buffer solution in the production method according to the present invention gives a crosslinked hyaluronan gel excellent in viscoelasticity. In particular, a higher alkali concentration during the crosslinking reaction can produce a gel having a higher elastic property against deformation.

Figure 5:
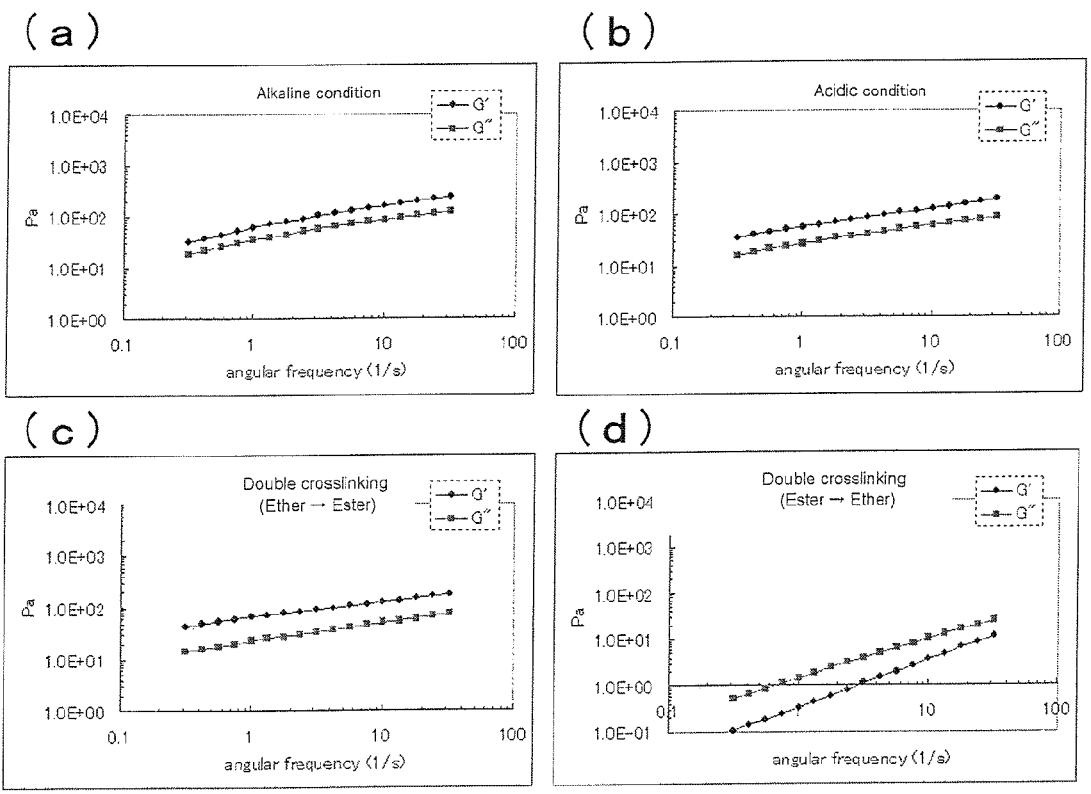
FIG. 5 includes graphs comparing dynamic viscoelasticity of the hyaluronan gels prepared in Examples 14 to 17 of the present invention ((a): Example 14, (b): Example 15, (c): Example 16, (d): Example 17).

In addition, the crosslinked hyaluronan gels shown in the above-described Example 14 and the blow-described Examples 15 to 17 were measured for dynamic viscoelasticity for comparing the characteristics. The results are shown in FIG. 5 (FIG. 5(a): Example 14, (b): Example 15, (c): Example 16, (d): Example 17). Incidentally, the dynamic viscoelasticity was measured according to the above-mentioned method.

Example 15

A hyaluronan powder (Biohyalo 12, molecular weight: 1200000, manufactured by Shiseido Co., Ltd.) was added and dispersed to give a concentration of 3.3 W/V % in 10 parts of a 0.001 N hydrochloric acid aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the hyaluronan powder was collected by filtration and then washed with ethanol and dried to give a swellable crosslinked hyaluronan powder. The powder was added in a physiological saline in a concentration of 2% by weight for swelling. The resulting crosslinked hyaluronan gel was used for viscoelasticity measurement.

Example 16

A hyaluronan powder (Biohyalo 12, molecular weight: 1200000, manufactured by Shiseido Co., Ltd.) was added and dispersed to give a concentration of 3.3 W/V % in 10 parts of a 0.001 N sodium hydroxide aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the mixture was filtered to collect the residue, and then the residue was washed with ethanol and dried to give a crosslinked hyaluronan powder.

Then, the crosslinked hyaluronan powder was added and dispersed to give a concentration of 3.3 W/V % in 10 parts of a 0.001 N hydrochloric acid aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the hyaluronan powder was collected by filtration and then washed with ethanol and dried to give a swellable crosslinked hyaluronan powder.

The powder was added in a physiological saline in a concentration of 2% by weight for swelling. The resulting crosslinked hyaluronan gel was used for viscoelasticity measurement.

Example 17

A hyaluronan powder (Biohyalo 12, molecular weight: 1200000, manufactured by Shiseido Co., Ltd.) was added and dispersed to give a concentration of 3.3 W/V % in 10 parts of a 0.001 N hydrochloric acid aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the mixture was filtered to collect the residue, and then the residue was washed with ethanol and dried to give a crosslinked hyaluronan powder.

Then, the hyaluronan powder was added and dispersed to give a concentration of 3.3 W/V % in 10 parts of a 0.001 N sodium hydroxide aqueous solution and 87 parts of ethanol, and 3 parts of a crosslinking agent (ethylene glycol diglycidyl ether: Denacol EX-810P, manufactured by Nagase Chemicals Co., Ltd.) was added to and mixed with the dispersion for conducting a crosslinking reaction at 90° C. for 1 hour. After the completion of the reaction, the hyaluronan powder was collected by filtration and then washed with ethanol and dried to give a swellable crosslinked hyaluronan powder. The powder was added in a physiological saline in a concentration of 2% by weight for swelling. The resulting crosslinked hyaluronan gel was used for viscoelasticity measurement.

As shown in FIG. 5, the water-swollen gels of both the crosslinked hyaluronan powder of Example 14 in which ether crosslinking was performed under alkaline conditions and the crosslinked hyaluronan powder of Example 15 in which ester crosslinking was performed under acidic conditions exhibited excellent viscoelasticity, without depending on angular frequency. Furthermore, the water-swollen gel of the double crosslinked hyaluronan powder prepared in Example 16 in which ester crosslinking was performed after ether crosslinking also similarly exhibited high viscoelasticity, but it was observed that the loss elastic modulus (G") was lower than those in Examples 14 and 15.

On the other hand, in Example 17 in which ether crosslinking was performed after ester crosslinking, the viscoelasticity was significantly decreased depending on the angular frequency.

From the above, it is obvious that the swellable crosslinked hyaluronan powder prepared by conducting the crosslinking reaction under alkaline conditions or acidic conditions in the production method according to the present invention provides a crosslinked hyaluronan gel excellent in viscoelasticity. In addition, the swellable crosslinked hyaluronan powder prepared by conducting a crosslinking reaction under alkaline conditions and then conducting a crosslinking reaction again under acidic conditions can provide a gel having a higher elastic property against deformation.

In addition, for example, when the crosslinked hyaluronan gel is used as an anti-wrinkle agent, the double crosslinked hyaluronan powder is thought to be more advantageous from the viewpoint of resistance to in vivo enzymatic degradation, in addition to the viscoelasticity.

What is claimed is:

1. A method for producing a swellable crosslinked hyaluronan powder having a swelling ratio in water of 500% or more, comprising mixing (a) a hyaluronan powder,
(b) a liquid medium containing a monovalent alcohol having 1 to 4 carbon atoms and having solubility of the hyaluronan powder of less than 0.1 g/L and
(c) a crosslinking agent, to cause a crosslinking reaction, and
wherein the hyaluronan powder is in a state dispersed in the liquid medium during the mixing step,
wherein the liquid medium is a solvent mixture of the monovalent alcohol and water, and
the mixing ratio of the monovalent alcohol to water is 99.9:0.1 to 65:35 as the mass ratio.

2. The method for producing the swellable crosslinked hyaluronan powder according to claim 1, wherein the water is an alkaline buffer solution or an acidic buffer solution.

3. The method for producing the swellable crosslinked hyaluronan powder according to claim 1, wherein the crosslinking agent is divinyl sulfone, 1,4-butanediol diglycidyl ether and/or ethylene glycol diglycidyl ether.

4. The method for producing the swellable crosslinked hyaluronan powder according to claim 1, wherein the monovalent alcohol is ethanol or 2-propanol.

5. A method for producing a swellable crosslinked hyaluronan powder having a swelling ratio in water of 500% or more, comprising
(1) mixing (a) a hyaluronan powder,
(b) a solvent containing a monovalent alcohol having 1 to 4 carbon atoms and an alkaline buffer solution and having solubility of the hyaluronan powder of less than 0.1 g/L, and
(c) a crosslinking agent, to cause a crosslinking reaction, and
wherein the hyaluronan powder is in a dispersed state in the solvent during the mixing step (1), and
(2) mixing (d) the product in the step (1),
(e) a solvent containing a monovalent alcohol having 1 to 4 carbon atoms and an acidic buffer solution and having a solubility of the hyaluronan powder of less than 0.1 g/L, and
(f) a crosslinking agent, to cause a crosslinking reaction, and wherein the product in the step (1) is in a state dispersed in the solvent during the mixing step (2), and
wherein the mixing ratio of the monovalent alcohol to the alkaline buffer solution or the acidic buffer solution is 99.9:0.1 to 65:35 as the mass ratio.

6. The method for producing the swellable crosslinked hyaluronan powder according to claim 5, wherein the crosslinking agent is divinyl sulfone, 1,4-butanediol diglycidyl ether, and/or ethylene glycol diglycidyl ether.

7. The method for producing the swellable crosslinked hyaluronan powder according to claim 5, wherein the monovalent alcohol is ethanol or 2-propanol.

8. A method for producing a swellable crosslinked hyaluronan powder having a swelling ratio in water of 500% or more, comprising:
crosslinking hyaluronan powder with a crosslinking agent in a liquid medium containing a monovalent alcohol having 1 to 4 carbon atoms and having solubility of the hyaluronan powder of less than 0.1 g/L, wherein the hyaluronan powder is in a state dispersed in the liquid medium during the crosslinking of the hyaluronan powder,
wherein the liquid medium is a solvent mixture of the monovalent alcohol and water, and
the mixing ratio of the monovalent alcohol to water is 99.9:0.1 to 65:35 as the mass ratio.

9. The method for producing the swellable crosslinked hyaluronan powder according to claim 8, wherein the water is an alkaline buffer solution or an acidic buffer solution.

10. The method for producing the swellable crosslinked hyaluronan powder according to claim 8, wherein the crosslinking agent is divinyl sulfone, 1,4-butanediol diglycidyl ether and/or ethylene glycol diglycidyl ether.

11. The method for producing the swellable crosslinked hyaluronan powder according to claim 8, wherein the monovalent alcohol is ethanol or 2-propanol.

* * * * *